US00PP17380P2

(12) United States Plant Patent
van Egmond

(10) Patent No.: US PP17,380 P2
(45) Date of Patent: Jan. 23, 2007

(54) ***PHLOX* PLANT NAMED 'SPINNERS'**

(50) Latin Name: *Phlox paniculata*
Varietal Denomination: Spinners

(75) Inventor: Martin van Egmond, Callantsoog (NL)

(73) Assignee: Green Works International, 't Zand (NL)

( * ) Notice: Subject to any disclaimer, the term of this patent is extended or adjusted under 35 U.S.C. 154(b) by 8 days.

(21) Appl. No.: 11/151,758

(22) Filed: Jun. 14, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Phlox* plant named 'Spinners', characterized by its upright and strong plant habit; freely basally branching habit; dense and bushy growth habit; thick and leathery foliage; attractive red-purple-colored flowers with white stripes; freely and continuous flowering habit; long flowering period; resistance to Powdery Mildew; and excellent garden performance.

1 Drawing Sheet

Botanical designation: *Phlox paniculata.*
Cultivar denomination: 'Spinners'.

BACKGROUND OF THE INVENTION

The present Invention relates to a new and distinct cultivar of *Phlox* plant, botanically known as *Phlox paniculata*, and hereinafter referred to by the cultivar name Spinners.

The new *Phlox* is a product of a planned breeding program conducted by the Inventor in Zwaanshoek, The Netherlands. The objective of the breeding program was to create new *Phlox* cultivars with attractive flower coloration, healthy foliage and resistance to Powdery Mildew.

The new *Phlox* originated from a cross-pollination made by the Inventor in 1999 in Callantsoog, The Netherlands of a proprietary selection of *Phlox paniculata* identified as code number 98421, not patented, as the female, or seed, parent with a proprietary selection of *Phlox paniculata* identified as code number 96562, not patented, as the male, or pollen, parent. The new *Phlox* was discovered and selected by the Inventor as a flowering plant within the progeny of the stated cross-pollination in a controlled environment in Callantsoog, The Netherlands in 2001.

Asexual reproduction of the new cultivar by terminal cuttings at Callantsoog, The Netherlands since 2001, has shown that the unique features of this new *Phlox* are stable and reproduced true to type in successive generations.

SUMMARY OF THE INVENTION

Plants of the cultivar Spinners have not been observed under all possible environmental conditions. The phenotype may vary somewhat with variations in environment such as temperature and light level without, however, any variance in genotype.

The following traits have been repeatedly observed and are determined to be the unique characteristics of 'Spinners'. These characteristics in combination distinguish 'Spinners' as a new and distinct cultivar of *Phlox:*

1. Upright and strong plant habit.
2. Freely basally branching habit; dense and bushy growth habit.

3. Thick and leathery foliage.
4. Attractive red purple-colored flowers with white stripes.
5. Freely and continuous flowering habit.
6. Long flowering period.
7. Resistant to Powdery Mildew.
8. Excellent garden performance.

Plants of the new *Phlox* differ primarily from plants of the parent selections in flower color. In addition, plants of the new *Phlox* have healthier foliage than plants of the male parent selection.

Plants of the new *Phlox* can be compared to the *Phlox paniculata* cultivar Bright Eyes, not patented. In side-by-side comparisons conducted in Zwaanshoek, The Netherlands, plants of the new *Phlox* differed from plants of the cultivar Bright Eyes primarily in flower color as plants of the cultivar Bright Eyes have pink-colored flowers with red purple-colored centers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ2 slightly from the color values cited in the detailed botanical description which more accurately describe the actual colors of the new *Phlox.*

The photograph at the top of the sheet is a close-up view of typical flowers of 'Spinners'.

The photograph at the bottom of the sheet comprises a side perspective view of a typical plants of 'Spinners'.

DETAILED BOTANICAL DESCRIPTION

The aforementioned photographs, following observations and measurements describe plants grown in Callantsoog, The Netherlands, in an outdoor nursery and under commercial production practices during the summer. Plants were about 13 weeks old when the photographs and description were taken. During the production of the plants, day temperatures ranged from 5 to 20° C. and night temperatures ranged from 2 to 12° C. In the following description, color references are made to The Royal Horticultural Society Colour Chart, 1995 Edition, except where general terms of ordinary dictionary significance are used.

Botanical classification: *Phlox paniculata* cultivar Spinners.

Parentage:

*Female parent.*—Proprietary selection of *Phlox paniculata* identified as code number 98421, not patented.

*Male parent.*—Proprietary selection of *Phlox paniculata* identified as code number 96562, not patented.

Propagation:

*Type.*—By terminal cuttings.

*Time to initiate roots, summer.*—About three weeks at 18° C.

*Time to initiate roots, winter.*—About five weeks at 18° C.

*Time to produce a rooted plant, summer.*—About four weeks at 18° C.

*Time to produce a rooted plant, winter.*—About six weeks at 18° C.

*Root description.*—Thick; well-branched.

Plant description:

*Plant form/habit.*—Upright and strong plant habit; conical; moderately vigorous growth habit. Freely basally branching habit, dense and bushy growth habit.

*Plant height.*—About 85 cm.

*Plant width* (*spread*).—About 40 cm.

*Lateral branches.*—Length: About 85 cm. Diameter: About 3 mm. Internode length: About 4 cm. Strength: Strong. Texture: Glabrous. Color: 187A; at nodes, 187B.

*Foliage description.*—Arrangement: Alternate, simple. Length, lower leaves: About 18 cm. Width, lower leaves: About 4.6 cm. Length, upper leaves: About 10.5 cm. Width, upper leaves: About 3.7 cm. Shape: Oblanceolate. Apex: Acuminate. Base: Obtuse. Margin: Entire. Texture, upper and lower surfaces: Leathery, thick; glabrous. Venation pattern: Pinnate. Color: Developing and fully expanded leaves, upper surface: 143A. Developing and fully expanded leaves, upper and lower surfaces: 144B. Venation, upper surface: 143A; towards midrib base, 144D. Venation, lower surface: 144D. Petiole: Length: About 2 mm. Diameter: About 2 mm. Texture, upper and lower surfaces: Glabrous. Color, upper and lower surfaces: 144D.

Flower description:

*Flower type/habit.*—Single, rounded salverform flowers arranged in terminal panicles; flowers face upright and outward. Panicles conical in shape. Freely flowering habit with about 18 to 25 flower buds and flowers per inflorescence and about 90 to 120 flowers per plant.

*Fragrance.*—Faint to moderate; sweet.

*Natural flowering season.*—Continuously flowering from July through September in The Netherlands. Flowers not persistent.

*Postproduction longevity.*—Flowers last about four days on the plant.

*Flower buds.*—Height: About 1.4 cm. Diameter: About 7 mm. Shape: Tubular. Color: 68D.

*Flowers.*—Diameter: About 2.5 cm. Depth: About 1.6 cm.

*Petals.*—Quantity per flower: Typically five in a single whorl; petals fused at the base into a narrow tube. Lobe length: About 1.5 cm. Lobe width: About 1 cm. Shape: Obovate to fan-shaped. Apex: Rounded. Margin: Entire. Aspect: Mostly flat; margins slightly curved upwards. Texture, upper and lower surfaces: Smooth, glabrous. Color: Developing petals, upper and lower surfaces: 68A with longitudinal stripes along the margins, 155D. Fully expanded petals, upper and lower surfaces: 70D with longitudinal stripes along the margins, 155D.

*Sepals.*—Quantity per flower: Typically five in a single whorl, fused; narrow tubular calyx. Length: About 5 mm. Width: About 1 mm. Shape: Apiculate. Apex: Acuminate. Texture, upper and lower surfaces: Smooth, glabrous. Color, upper and lower surfaces: Close to 144A.

*Reproductive organs.*—Stamens: Quantity per flower: Typically five; fused with petals in tube. Anther shape: Oblong. Anther length: About 0.5 mm. Anther color: 2D. Pollen amount: Moderate. Pollen color: 2D. Pistils: Quantity per flower: Typically one. Pistil length: About 1 cm. Stigma shape: Bi-parted. Stigma color: 154D. Style length: About 1.4 cm. Style color: 154D. Ovary color: 142C.

*Seed/fruit.*—Seed and fruit development have not been observed.

Disease/pest resistance: Plants of the new *Phlox* have been noted to be resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and are winter hardy in The Netherlands.

It is claimed:

1. A new and distinct cultivar of *Phlox* plant named 'Spinners', as illustrated and described.

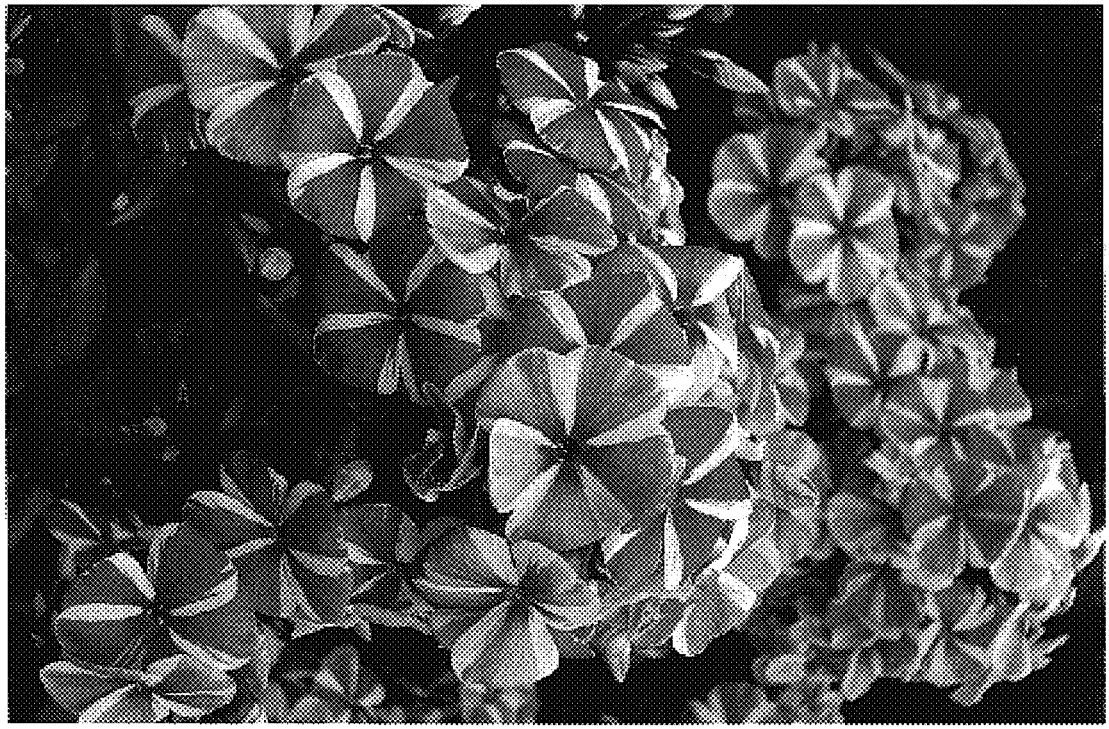
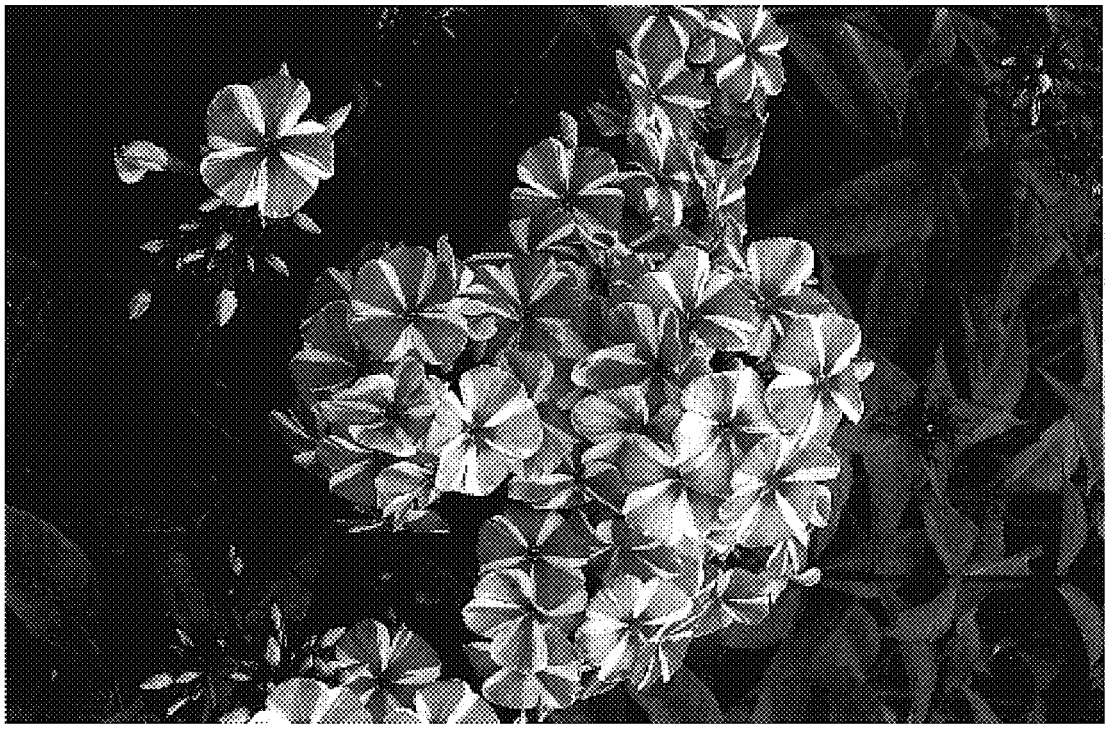

* * * * *